(12) United States Patent
Goodfellow et al.

(10) Patent No.: US 9,770,249 B2
(45) Date of Patent: Sep. 26, 2017

(54) ROTARY MILL

(75) Inventors: John William Goodfellow, Basingstoke (GB); David Wycliffe Murray, Oxford (GB); Christopher Alexander Dodd, Oxford (GB); John Joseph O'Connor, Oxford (GB); Mona Alinejad, London (GB); Russell Lloyd, Wiltshire (GB); Duncan Andrew Ridley, Bristol (GB); Colin Hunsley, legal representative, Basingstoke (GB); Anna Elizabeth Burnside, legal representative, Oxford (GB); Robert Maurice Kirtland, legal representative, Oxford (GB)

(73) Assignee: Biomet UK Healthcare Limited (GB)

( * ) Notice: Subject to any disclaimer, the term of this patent is extended or adjusted under 35 U.S.C. 154(b) by 851 days.

(21) Appl. No.: 13/981,949

(22) PCT Filed: Jan. 26, 2012
(Under 37 CFR 1.47)

(86) PCT No.: PCT/GB2012/050159
§ 371 (c)(1),
(2), (4) Date: Mar. 3, 2014

(87) PCT Pub. No.: WO2012/101441
PCT Pub. Date: Aug. 2, 2012

(65) Prior Publication Data
US 2015/0066034 A1 Mar. 5, 2015

(30) Foreign Application Priority Data

Jan. 27, 2011 (GB) .................................. 1101377.8

(51) Int. Cl.
*A61B 17/16* (2006.01)
*A61B 17/17* (2006.01)
(Continued)

(52) U.S. Cl.
CPC .......... *A61B 17/1675* (2013.01); *A61B 17/16* (2013.01); *A61B 17/1613* (2013.01);
(Continued)

(58) Field of Classification Search
CPC ............ A61B 17/16; A61B 2017/1602; A61B 17/1613; A61B 17/1615; A61B 17/1617;
(Continued)

(56) References Cited

U.S. PATENT DOCUMENTS

| 4,193,721 A | 3/1980 | Hougen |
| 5,002,547 A | 3/1991 | Poggie et al. |

(Continued)

FOREIGN PATENT DOCUMENTS

| CA | 2825675 C | 10/2016 |
| EP | 1374804 A2 | 1/2004 |

(Continued)

OTHER PUBLICATIONS

"Canada Application Serial No. 2,825,675, Office Action mailed Jul. 20, 2015", 5 pgs.
(Continued)

*Primary Examiner* — Larry E Waggle, Jr.
(74) *Attorney, Agent, or Firm* — Schwegman Lundberg & Woessner, P.A.

(57) ABSTRACT

A rotary mill is disclosed comprising a body portion (4) having a milling surface (10) and a central bore (20) extending along an axis of rotation (18) of the body portion (4); and a guide portion (6) having a guide body (22) and a guide peg (24) extending from the guide body (22), the guide peg (24) operable to be received in the central bore (20) of the body portion (4), the guide body (22) having at least one alignment feature (28, 30) which is the same as that of a prosthesis component. A method of implanting a unicondylar femoral component is also disclosed, the method
(Continued)

comprising, a) reaming the femoral condylar surface to accept the unicondylar femoral component; b) drilling peg holes for affixing the unicondylar femoral component; c) affixing a guide portion of a rotary mill onto the prepared condylar surface using the drilled peg holes; d) reaming a portion of bone anterior to the affixed guide portion; e) removing the guide portion from the bone; and f) affixing a unicondylar femoral component to the prepared condylar surface.

37 Claims, 6 Drawing Sheets

(51) Int. Cl.
*A61F 2/46* (2006.01)
*A61F 2/38* (2006.01)

(52) U.S. Cl.
CPC ...... *A61B 17/1615* (2013.01); *A61B 17/1617* (2013.01); *A61B 17/1662* (2013.01); *A61B 17/17* (2013.01); *A61B 17/1739* (2013.01); *A61B 17/1764* (2013.01); *A61F 2/3859* (2013.01); *A61F 2/4684* (2013.01); *A61B 2017/1602* (2013.01); *A61F 2002/3863* (2013.01)

(58) Field of Classification Search
CPC . A61B 17/1662; A61B 17/1675; A61B 17/17; A61B 17/1739; A61B 17/1764; A61F 2/4684
See application file for complete search history.

(56) References Cited

U.S. PATENT DOCUMENTS

| | | | | |
|---|---|---|---|---|
| 5,171,313 | A * | 12/1992 | Salyer | A61B 17/1617 606/100 |
| 5,314,482 | A * | 5/1994 | Goodfellow | A61B 17/1637 606/88 |
| 5,336,226 | A * | 8/1994 | McDaniel | A61B 17/1666 606/79 |
| 6,322,564 | B1 | 11/2001 | Surma | |
| 6,827,741 | B2 * | 12/2004 | Reeder | A61B 17/15 606/180 |
| 7,306,607 | B2 * | 12/2007 | Metzger | A61B 17/155 606/79 |
| 7,527,631 | B2 * | 5/2009 | Maroney | A61B 90/06 606/102 |
| 7,695,520 | B2 * | 4/2010 | Metzger | A61B 17/1675 623/20.35 |
| 2006/0015111 | A1 | 1/2006 | Fenton | |
| 2007/0203500 | A1 | 8/2007 | Gordon et al. | |
| 2007/0276394 | A1 | 11/2007 | Johnson et al. | |
| 2007/0282451 | A1 | 12/2007 | Metzger et al. | |
| 2010/0042103 | A1 | 2/2010 | Rasmussen | |
| 2010/0198224 | A1 | 8/2010 | Metzger | |
| 2010/0222781 | A1* | 9/2010 | Collazo | A61B 17/1764 606/89 |

FOREIGN PATENT DOCUMENTS

| | | |
|---|---|---|
| EP | 1864617 A2 | 12/2007 |
| EP | 2667797 A1 | 12/2013 |
| JP | 61127913 A | 6/1986 |
| JP | 01250250 A | 10/1989 |
| JP | 01308555 A | 12/1989 |
| JP | 08502681 A | 3/1996 |
| JP | 2005046625 A | 2/2005 |
| JP | 5991549 B2 | 9/2016 |
| WO | WO2012101441 A1 | 8/2012 |

OTHER PUBLICATIONS

"Canada Application Serial No. 2,887,742, Office Action mailed Jul. 15, 2015", 4 pgs.
"Canadian Application Serial No. 2,825,675, Office Action mailed Jul. 20, 2015", 5 pgs.
"Canadian Application Serial No. 2,887,742, Office Action mailed May 24, 2016", 3 pgs.
"Canadian Application Serial No. 2,887,742, Office Action mailed Jul. 15, 2015", 4 pgs.
"Canadian Application Serial No. 2,887,742, Response filed Jan. 15, 2016 to Office Action mailed Jul. 15, 2015", 4 pgs.
"Japanese Application Serial No. 2013-550950, Office Action mailed Dec. 7, 2015", 3 pgs.
"Japanese Application Serial No. 2013-550950, Response filed Mar. 7, 2016 to Office Action mailed Dec. 7, 2015", with English translation of claims, 6 pgs.
Great Britain Search Report and Written Opinion mailed Apr. 14, 2011 for GBSN 1101377.8 filed Jan. 27, 2011.
International Preliminary Report on Patentability mailed Aug. 8, 2013 for PCT/GB2012/050159 claiming benefit of GBSN 1101377.8 filed Jan. 27, 2011.
International Search Report and Written Opinion mailed Apr. 3, 2012 for PCT/GB2012/050159 claiming benefit of GBSN 1101377.8 filed Jan. 27, 2011.
International Search Report for PCT/GB2012/050159, mailed Apr. 3, 2012; ISA/EP.
"Canadian Application Serial No. 2,887,742, Response filed Oct. 25, 2016 to Office Action mailed May 24, 2016", 3 pgs.
"United Kingdom Application Serial No. 1101377.8, Office Action mailed Sep. 27, 2016", 3 pgs.
"Canadian Application Serial No. 2,887,742, Notice of Allowance dated Jan. 26, 2017", 1 pg.
"United Kingdom Application Serial No. 1101377.8, Notice of Decision to Grant dated Mar. 28, 2017", 2 pgs.
"United Kingdom Application Serial No. 1101377.8, Office Action dated Feb. 16, 2017", 2 pgs.
"United Kingdom Application Serial No. 1101377.8, Office Action dated Dec. 20, 2016", 2 pgs.
"United Kingdom Application Serial No. 1101377.8, Response filed Feb. 9, 2017 to Office Action dated Dec. 26, 2016", 7 pgs.
"United Kingdom Application Serial No. 1101377.8, Response filed Nov. 28, 2016 to Office Action dated Sep. 27, 2016", 14 pgs.

* cited by examiner

ROTARY MILL

CROSS-REFERENCE TO RELATED APPLICATIONS

This application is a 371 U. S. National Stage of International Application No. PCT/GB2012/050159, filed on Jan. 26, 2012 and published as WO 2012/101441 A1 on Aug. 2, 2012. This application claims priority to British Patent Application No. 1101377.8, filed on Jan. 27, 2011. The disclosures of the above applications are incorporated herein by reference in their entirety.

The present invention relates to rotary mills and similar rotary cutting devices and particularly but not exclusively relates to rotary mills for use in preparing a bone for total or partial joint replacement surgery.

BACKGROUND

It is known to replace all or part of a knee joint in which the joint surfaces have deteriorated, for example as a result of osteoarthritis. Such deterioration usually starts in only one of the tibeo-femoral compartments and may spread to the other at a later stage. Replacement of only one compartment of the joint can therefore be sufficient to provide prolonged relief from symptoms. Damaged bearing surfaces are replaced by a unicompartmental prosthesis which comprises a femoral implant and a tibial implant (usually metallic), which interface through a (polyethylene) bearing component disposed between the two implants.

A unicompartmental or partial knee replacement (PKR) helps to conserve undamaged bone and restores more natural movement to the joint. Also, owing to the small size of the prosthesis, the surgery may be less invasive than a total knee replacement (TKR). However, the design requirements for partial knee replacement prostheses are more demanding than those for total knee replacement prostheses. Unlike in a total knee replacement, where one or more ligaments can be discarded and the mechanics of the knee can be simplified, in a unicompartmental knee replacement, all the ligaments in the joint must be retained and restored to their natural tensions and the bearing component must be completely unconstrained.

During articulation of the knee, and particularly when the joint is at full extension, the bearing component can impinge on femoral condylar bone tissue superior to the femoral implant, as illustrated in FIG. 1. Such impingement of the polyethylene bearing component onto the bone can lead to post operative pain, damage to the bearing, increased wear and eventual failure. It is therefore essential to remove a sufficient amount of anterior bone on the femoral condyle during the implantation procedure to prevent such impingement from occurring.

Orthopaedic surgeons conventionally use a bone chisel to manually remove the anterior bone. However, such a manual procedure can easily be forgotten during surgery and, even when carefully completed, results in an undesirable non uniform bone edge and in the removal of an uncertain and varying amount of bone.

SUMMARY OF INVENTION

According to the present invention, there is provided a rotary mill comprising a body portion having a milling surface and a central bore extending along the rotary axis of the body portion; and a guide portion having a guide body and a guide peg extending from the guide body, the guide peg operable to be received in the central bore of the body portion, the guide body having at least one alignment feature which is the same as that of a prosthesis component.

By forming the guide body to have at least one alignment feature which is the same as that of a prosthesis component, the guide portion can be applied to the bone and fixed in place using the pre prepared fixation features that will hold the prosthesis component in place (for example peg holes or a recess for a flange). The guide body thus provides a precise reference of the final location of the prosthesis component to be implanted. The guide peg thus guides the body portion to mill an area of bone that is in a precise and predetermined location with respect to the eventually implanted prosthesis component.

A further advantage to the guide body being formed in this manner is that no additional bone must be removed in order for it to be fixed on the bone surface. The guide portion, having at least one alignment feature which is the same as that of a prosthesis component, can fit into the necessary recesses already formed in the bone to accommodate the final prosthesis component. This is in contrast to conventional guided mills which require a dedicated hole to be drilled to accommodate a separate guide rod.

The at least one alignment feature may be an attachment peg or may be a pair of attachment pegs. The attachment pegs may be operable to be received in pre prepared prosthesis peg holes.

The guide body may have substantially the form of a trial prosthesis component and may in fact comprise a trial prosthesis component.

The guide body may include at least one nodule, protruding from a surface of the guide body and operable to abut a corresponding abutment surface on the body portion. The nodules may thus act as depth stops to ensure a precise amount of bone is removed and avoid excessive bone removal.

The guide peg may comprise an abutment surface operable to abut a corresponding abutment surface in the central bore of the body portion. The guide peg may thus not only act to guide the angle at which the body portion mills bone surface but may also act as a depth stop to limit bone removal.

The abutment surface may comprise a distal surface of the peg or the abutment surface may comprise an outwardly projecting annular shoulder.

The corresponding abutment surface of the central bore may comprise a base of the bore or may comprise an inwardly projecting annular shoulder.

The guide peg may project from a predetermined region of, and at a predetermined angle to the guide body. In this manner the region of bone to be removed may be precisely determined and fixed by the construction of the guide portion, facilitating accuracy and repeatability of milling.

The guide peg may be adjustable on the guide body, allowing the surgeon a degree of freedom in selection of the milled area, and to accommodate for different patient geometries.

The guide body may be operable to be connected to additional surgical tools, thus facilitating and providing reference for additional bone removal steps.

The guide body may comprise a trial femoral prosthesis component which may be a trial unicondylar femoral prosthesis component.

The guide peg may project from an anterior portion of the guide body and may be operable to guide reaming of a region superior to the anterior edge of the guide body.

The guide peg may project from the guide body at an angle of between 25 and 40 degrees to the axis of the attachment peg. The angle may vary according to the size of the rotary mill.

The guide body may be operable to be connected to a posterior osteophyte guide.

The rotary mill may further comprise additional guide portions, each guide portion being of a different size so as to match differently sized prosthesis components that are employed for patents of differing sizes.

The rotary mill may further comprise additional guide portions, each guide portion having a different length, and or angle of extension of guide peg, thus also accommodating different patent geometries.

The body portion of the rotary mill may comprise a rotary body and a guide shaft at least partially received within the rotary body.

The guide shaft may comprise an inner portion telescopically received within an outer portion and a biasing element acting between the inner and outer portions.

The guide shaft may be received within an axial bore which may be formed in the rotary body. The bore may be a blind bore.

The biasing element may comprise a spring which may be mounted about the inner portion of the guide shaft.

The body portion may further comprise cooperating protrusions formed on the rotary body and the outer portion of the guide shaft, operable to engage one another as a depth stop.

The cooperating protrusions may comprise annular shoulders which may be formed on an inner surface of the rotary body and an outer surface of the outer portion of the guide shaft.

The outer portion of the guide shaft may comprise a substantially hollow shaft, a distal end of which may comprise the central bore of the body portion, operable to receive the guide peg.

The cutting surface of the body portion may be formed on an annular cutting tool which may be removably attached to the rotary body.

According to another aspect of the present invention, there is provided a method of implanting a unicondylar femoral component comprising,
a) reaming the femoral condylar surface to accept the unicondylar femoral component;
b) drilling peg holes for affixing the unicondylar femoral component;
c) affixing a guide portion of a rotary mill onto the prepared condylar surface using the drilled peg holes;
d) reaming a portion of bone anterior to the affixed guide portion;
e) removing the guide portion from the bone; and
f) affixing a unicondylar femoral component to the prepared condylar surface.

The rotary mill may be a rotary mill according to the first aspect of the present invention.

According to another aspect of the present invention, there is provided a rotary cutting tool comprising a rotary body having a cutting surface and a guide shaft at least partially received within the rotary body, wherein the guide shaft comprises an inner portion telescopically received within an outer portion, and a biasing element acting between the inner and outer portions.

The biasing element of the tool thus acts to damp the telescoping motion of the guide shaft and hence, when received within the rotary body, damps progression of the rotary body along the guide shaft. This damping action can assist a surgeon with fine control of cutting or milling operations.

The guide shaft may be received within an axial bore formed on the rotary body. The bore may be a blind bore.

The rotary cutting tool may further comprise cooperating protrusions formed on the rotary body and the outer portion of the guide shaft, which protrusions may be operable to engage one another as a depth stop.

The protrusions may for example comprise annular shoulders which may be formed on an inside surface of the rotary body and an outer surface of the outer portion of the guide shaft.

The biasing element may comprise a spring. The spring may be mounted about the inner portion of the guide shaft. The spring may act between an end of the outer portion of the guide shaft and an end cap formed on the inner portion of the guide shaft. The end cap may be formed by an end of the axial bore in which the guide shaft is received.

The outer portion of the guide shaft may comprise a hollow shaft, a first end of which may receive the inner portion and a second end of which may be operable to receive a guide peg.

The cutting surface of the rotary cutting tool may be formed on an annular cutting plate which may be removably attached to the rotary body.

An end of the rotary body may terminate in an annular receiving plate, which may be operable to engage the cutting plate.

The rotary cutting tool may further comprise cooperating formations on the receiving plate and cutting plate, which may be operable to secure the cutting plate to the receiving plate.

The cooperating formations may comprise protrusions, for example screw heads, and appropriately shaped recesses. The formations may alternatively or further comprise magnetic elements.

Another end of the rotary body may terminate in a drive shaft which may be operable to engage a drive element such as a rotary drill.

BRIEF DESCRIPTION OF DRAWINGS

For a better understanding of the present invention, and to show more clearly how it may be carried into effect, reference will now be made, by way of example, to the following drawings, in which.

DETAILED DESCRIPTION

Figure 4:
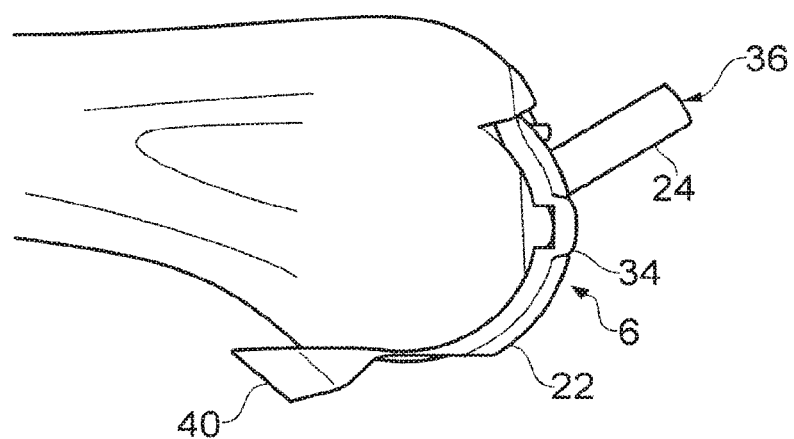
FIG. 4 shows a guide portion of a rotary mill in position on a femur.
Figure 2:
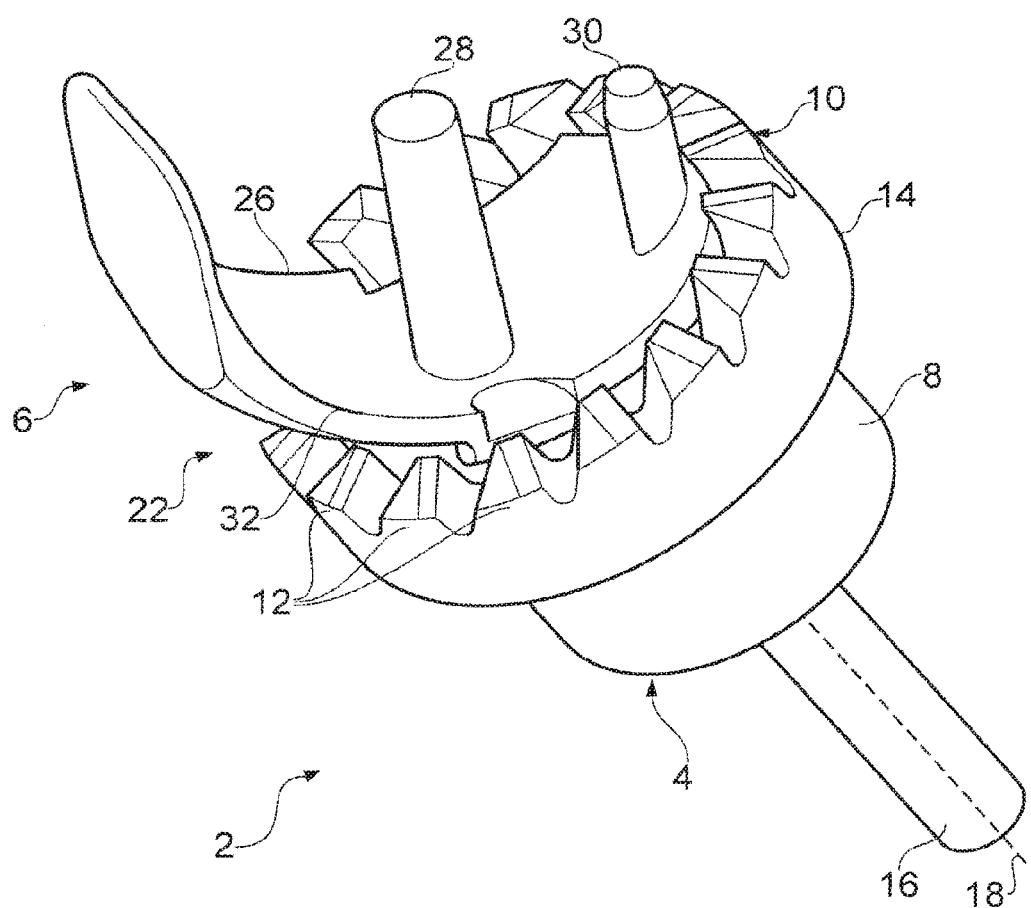
FIG. 2 is a perspective view of a rotary mill.
Figure 3:
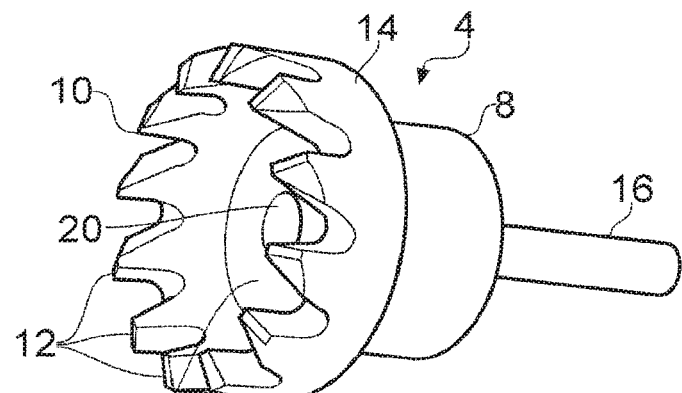
FIG. 3 is a perspective view of a body portion of a rotary mill.

With reference to FIGS. 2 to 4, a rotary mill 2 comprises a body portion 4 and a guide portion 6. The body portion 4 comprises a rotary body 8 that terminates at one end in an annular milling surface 10. The milling surface comprises a series of milling teeth 12 that extend from the surface 10. In the illustrated embodiment, the milling surface 10 is formed on an annular shoulder 14 that protrudes outwardly from the rotary body 8. An abutment surface 15 extends radially inwardly of the projecting milling surface 10. At a second end of the rotary body 8 an integral shank 16 extends along an axis of rotation 18 of the rotary body. The shank 16 is suitable for attachment to the chuck of a surgical drill (not shown). A bore 20 extends through the rotary body 8 along the axis of rotation 18 of the rotary body 8.

Figure 6:
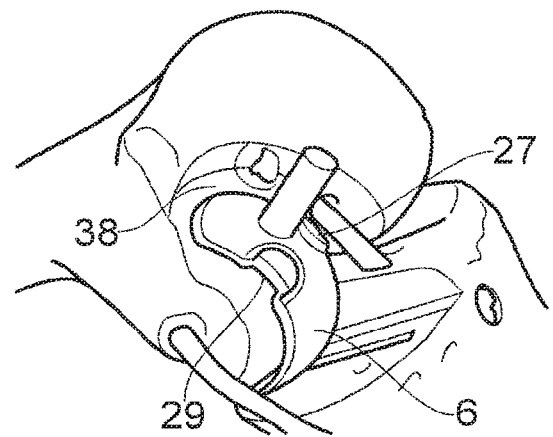
FIG. 6 illustrates bone removal by a rotary mill.

The guide portion 6 comprises a guide body 22 and a guide peg 24. The guide body 22 comprises a trail unicondylar femoral prosthesis component. The guide body thus comprises a curved condylar plate 26 and two attachment pegs 28, 30. The attachment pegs 28, 30 protrude from a bone contacting surface 32 of the condylar plate 26 at locations and angles precisely matching those of a similarly sized prosthesis component. The guide body can thus be attached to a prepared femoral condylar surface in the same manner and using the same drilled peg holes as for a prosthesis component. In this manner, the attachment pegs 28, 30 serve to align the guide body with the eventual location of the femoral prosthesis, referencing off the pre prepared drilled femoral peg holes. The guide peg 24 is a cylindrical peg that protrudes from an opposite, outer surface 34 of the condylar plate 26. The guide peg 24 extends from an anterior portion of the condylar plate 26 along an axis that is substantially normal to the adjacent condylar plate surface 34. The guide peg 24 projects at an angle of between 25 and 40 degrees to the axis of the attachment pegs. The precise angle is selected according to the size of the guide portion and associated anatomy, as discussed in further detail below. The guide peg 24 is dimensioned to be slidably and rotatably received within the central bore 20 of the rotary body 8. With reference also to FIG. 6, two nodules 27, 29 protrude from the outer surface 34 of the condylar plate 26. The nodules 27, 29 are formed on opposite sides of the anterior portion of the condylar plate 26, in the region of the guide peg 24.

Figure 5:
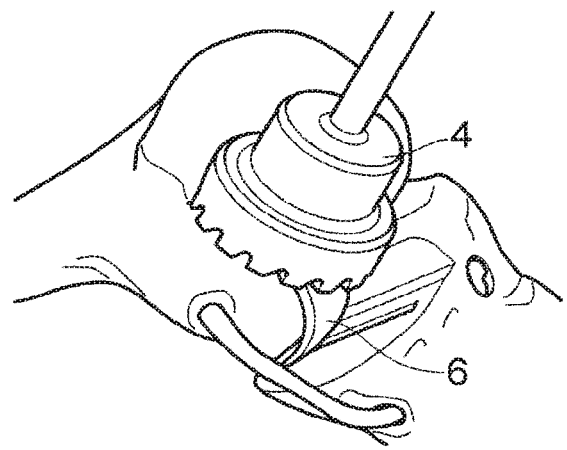
FIG. 5 shows a rotary mill in position on a femur.

The rotary mill 2 is used to remove anterior bone on the femoral condyle prior to implantation of a unicondylar femoral prosthesis. First, the condylar surface is prepared to receive the prosthesis, including resection of the entire condylar surface and drilling of femoral peg holes. The guide portion 6 of the rotary mill 2 is then fixed on the femoral condyle by inserting the attachment pegs 28, 30 into the pre drilled femoral peg holes. The guide portion 6 can be seen in position on the femoral condyle in FIG. 4. The body portion 4 is then seated on the guide portion 4, the guide peg 24 being receiving within the bore 20 of the rotary body 8. The shank 16 of the body portion is then attached to a surgical drill and the body portion 4 is guided to mill the bone superior to the anterior edge of the condylar plate 26 of the guide portion. The guide peg 24 guides the orientation of the body portion 4, ensuring that the milling surface 10 removes the bone tissue from the correct location. The body portion 4 advances along the guide peg 24 as bone tissue is removed. As the body portion 4 advances, the nodules 27, 29 act as stop pegs, upper surfaces of the nodules 27, 29 abutting the stop surface 15 that extends radially inwardly from the annular milling surface 10 and preventing further movement of the body portion 4, thus limiting the amount of bone that is removed. The body portion 4 is dimensioned so as to ream only the anterior bone superior to the guide portion. As can be seen from FIGS. 5 and 6, the milling surface 10 does not disturb the adjacent soft tissues and so causes minimal damage or disruption to the surrounding structures, removing only that bone which is desired to be removed. As illustrated particularly in FIG. 5, the guide peg 24 is angled such that, when fully seated on the guide peg 24, the body portion 4 has only reamed the bone superior to the anterior edge of the guide portion 6. The reamed area of bone can be seen at area 38 on FIG. 6.

Additional tools can then be attached to the guide portion if necessary. For example, a posterior osteophyte guide 40 can be attached posteriorly to the guide portion 6. The osteophyte guide is a slotted tool that may be used to guide a chisel to remove osteophytes from the posterior area of the femoral condyle, helping to prevent femoral loosening.

Figure 1:
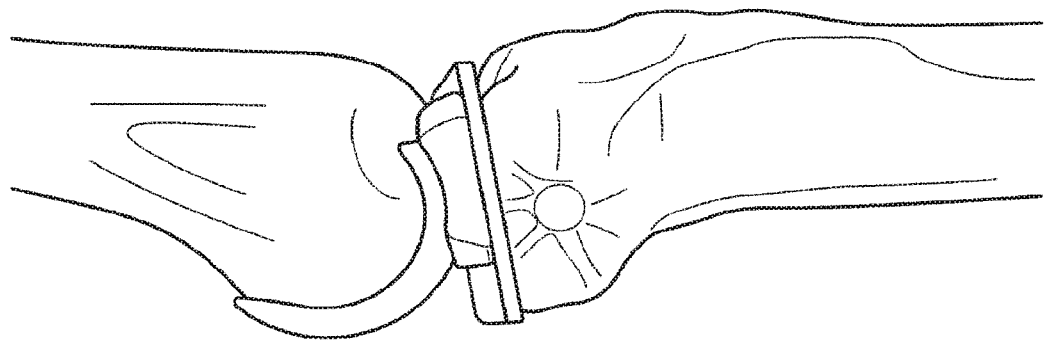
FIG. 1 shows impingement of a meniscal bearing on anterior femoral bone.
Figure 7:
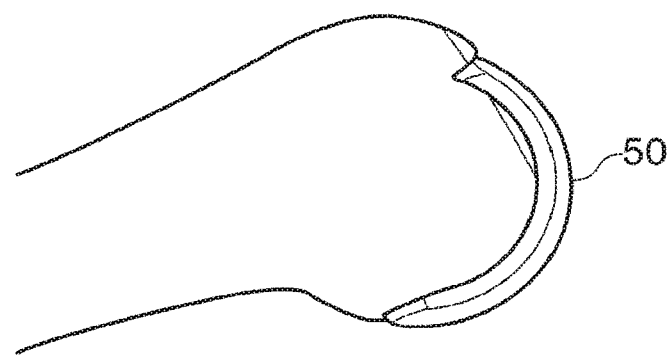
FIGS. 7 and 8 illustrate prosthesis components in position on a femur, with and without bone removal.
Figure 8:
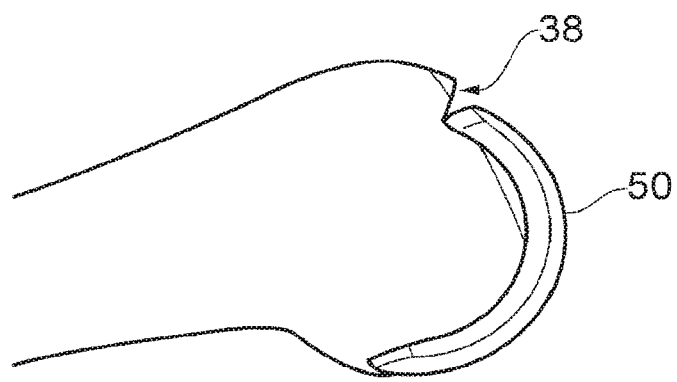
Figure 9:
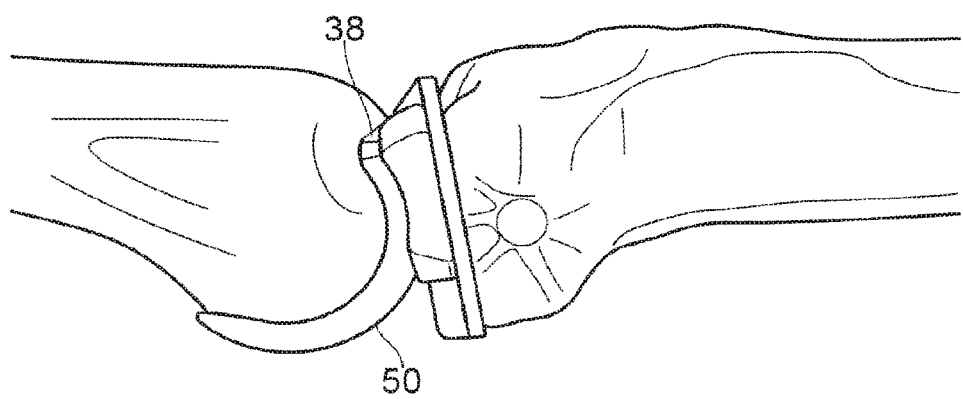
FIG. 9 illustrates an implanted unicondylar prosthesis.

Once all necessary bone removal has been completed, the guide portion 6 of the rotary mill 2 is removed and the appropriate prosthesis component is implanted. FIGS. 7 and 8 illustrate the area 38 of bone that is removed by the rotary mill 2. On FIG. 8, this area 38 can be seen immediately superior to the femoral prosthesis component 50. On FIG. 7, the rotary mill 2 has not been used and bone tissue remains superior to the prosthesis component 50. This bone tissue will cause impingement of the meniscal component, as illustrated in FIG. 1. In contrast, and as illustrated in FIG. 9, when the mill has been used to remove bone over the desired area 38, no impingement of the meniscal component is seen, even with the knee in full extension.

It is envisaged that the guide peg 24 may be integral with the guide body 22 or may be detachable from, or adjustable relative to, the guide body 22, so as to allow limited adjustment of the angle of the guide peg 24 or of the height of the guide peg 24. Such adjustment allows a degree of flexibility to the surgeon in tailoring the rotary mill 2 to the precise needs of individual patients. For example, if it is desired to remove less than the usual amount of bone, the guide peg 24 may be caused to protrude further from the surface of the condylar plate 26. In this instance, the guide peg 24 also acts as a stop peg, the end surface 36 of the guide peg 24 contacting the base (not shown) of the bore 20 and preventing further movement. The guide peg may be caused to protrude to such an extent that it is engages as a stop peg before the stop surface 15 of the body portion 4 contacts the nodules 27, 29 of the guide body. It is also envisaged that the guide portion 6 of the rotary mill will be provided as merely one of several available guide portions, each being of a different size to accommodate different sizes of knee. Thus, each size of prosthesis may have an associated guide portion 6 of the appropriate size. Each guide portion 6 will have a suitable guide peg, of a height and at an angle that is determined to be most appropriate for the associated prosthesis.

Figure 10:
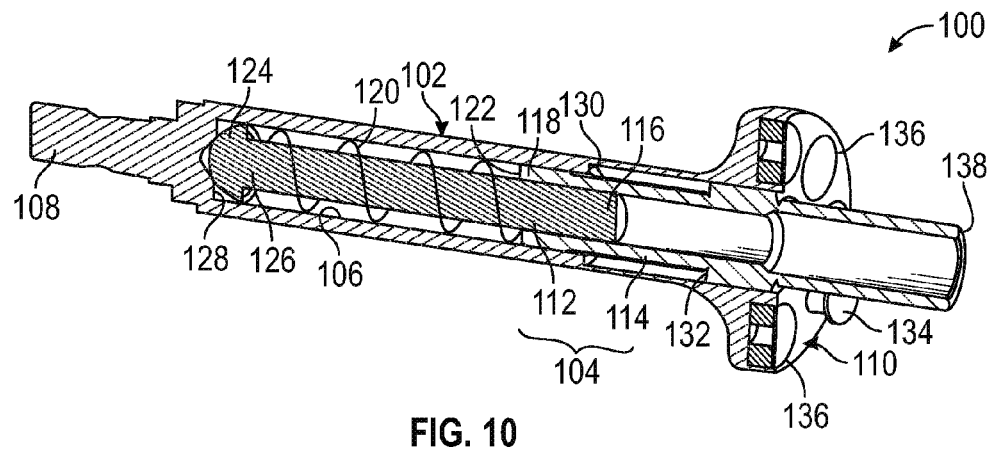
FIG. 10 is a sectional view of a rotary cutting tool.
Figure 11:
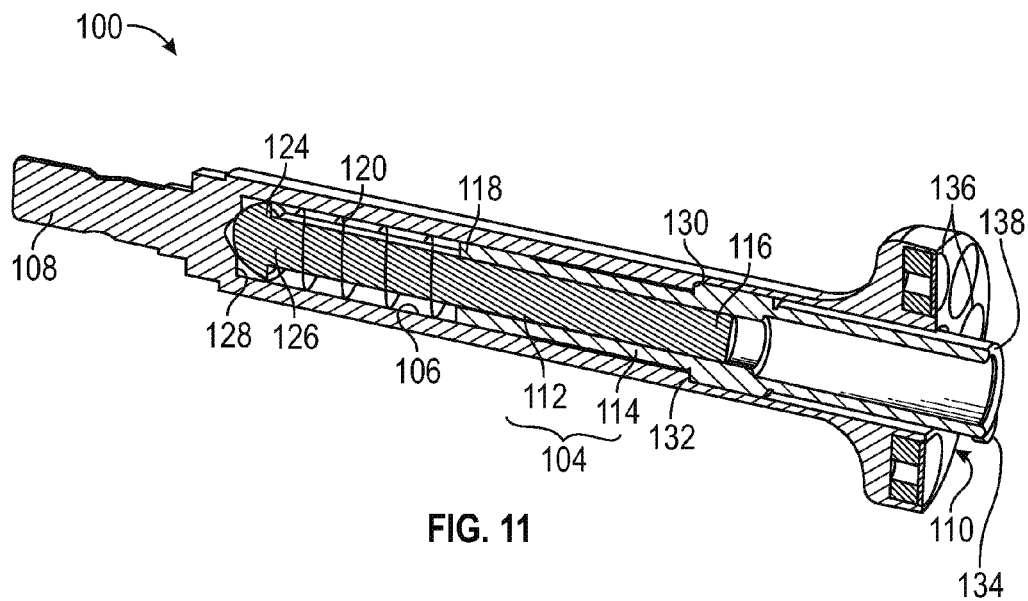
FIG. 11 is a sectional view of the tool of FIG. 10 in a compressed condition.

It will be appreciated that the guide portion 6 may be employed together with other embodiments of body portion 4, including a range of rotary cutting devices. One embodiment of rotary cutting tool with which the guide portion 6 may be employed is illustrated in FIGS. 10 and 11. The rotary cutting tool 100 comprises a rotary body 102 and a guide shaft 104. The guide shaft 104 is at least partially received within a blind axial bore 106 formed within the rotary body 102. A closed proximal end (towards the left in the Figures) of the rotary body 102 terminates in a drive shaft 108, operable to be received within the chuck of a surgical drill (not shown). An open distal end of the rotary body 102 flares outwards to terminate in an annular receiving plate 110 extending about the opening of the axial bore 106 and described in further detail below.

The guide shaft 104 comprises an inner portion 112 and an outer portion 114. The inner portion 112 comprises a solid shaft a distal end 116 of which is telescopically received within a proximal end 118 of the outer portion 114. The outer portion 114 comprises a substantially hollow shaft. A biasing spring 120 is mounted about the inner portion 112 of the guide shaft 104. The spring 120 rests at one end on the annular end surface 122 of the proximal end 118 of the outer portion 114. The other end of the spring 120 engages on an end cap 124 formed on a proximal end 126 of the inner portion 112. In an alternative embodiment (not shown) the spring 120 may engage on the blind end 128 of the axial bore 106 in which the guide shaft 104 is received.

The guide shaft is received freely within the bore 106 of the rotary body 102. An annular shoulder 130 is formed on the inner surface of the bore 106, dividing the bore into a distal section and a proximal section, the distal section being of larger inside diameter than the proximal section. A corresponding annular shoulder 132 is formed on the outer surface of the outer portion 114 of the guide shaft, dividing the outer portion into proximal and distal sections, the distal section being of larger outside diameter than the proximal section. The corresponding annular shoulders 130, 132 function as a depth stop, preventing the outer portion 114 of the guide shaft 104 from being received into the rotary body 102 beyond a certain point. This position is illustrated in FIG. 11. The larger diameter distal section of the outer portion 114 of the guide shaft may also serve to centre the guide shaft within the bore 106 of the rotary body 102.

Referring particularly to FIG. 10, the annular receiving plate 110 comprises a series of formations, operable to releasably engage an annular cutting plate (not shown). The formations comprise at least one screw head 134 and a plurality of magnets 136, the magnets being recessed into the annular receiving plate so as to present a smooth surface. The annular cutting plate (not shown) comprises an annular cutting surface, similar to that described above with reference to the body portion 6, and an opposed annular engaging surface. The annular engaging surface comprises corresponding recesses and magnetic elements enabling the cutting plate to be releasably yet securely attached to the receiving plate 110 of the rotary body.

In use, the rotary cutting tool 100 is first assembled and then placed over the guide peg 24 of the guide portion 6. The guide peg 24 is received within the hollow outer portion 114 of the guide shaft until a distal end 138 of the outer portion 114 is seated against the surface 34 from which the guide peg 24 protrudes. The rotary body 102 is then connected to a surgical drill (not shown) via the drive shaft 108 and the rotary tool is guided to mill away the desired area of bone. During the cutting operation, the outer portion 114 of the guide shaft 104 remains seated in position over the guide peg 24. Downward pressure applied to the rotary body engages the blind end 128 of the bore 106 against the end cap of the inner portion 112 of the guide shaft 104, causing the inner portion 112 to be pushed further into the outer portion 114. This action compresses the spring 120 acting between the inner and outer portions. In this manner, the spring 120 damps the downward motion of the rotary body, assisting the control of the surgeon and thus increasing the ease with which the tool may be employed. The inner portion 112 of the guide shaft 104 continues to slide further into the outer portion 114 until the annular shoulder 130 on the rotary body 102 engages the annular shoulder 132 on the outer portion 114 of the guide shaft. At this point the rotary body cannot travel any further towards the bone and the drilling action is ceased. In this manner, the annular shoulders act as a depth stop, preventing over reaming of the bone.

It will be appreciated that the present invention provides a means for accurately, predictably and repeatably removing a targeted area of bone from the femoral condyle. The amount of bone removed is determined by the precise angle and height of the guide peg 24. These aspects of the guide peg 24 are determined when the guide portion 6 is initially formed and can thus be carefully assessed and fixed so as to guide milling of precisely the correct amount of bone for the associated prosthesis. The present invention is also bone conserving, requiring no additional drill hole for a guide rod, as is conventionally required for a guided mill. By fastening to the bone using the existing femoral peg holes, the guide portion 6 makes use of existing features, and requires no additional bone removal for fixation. The femoral peg holes in fact determine the eventual location of the milled bone, as they provide the location for the guide portion 6. As these peg holes also provide location for the final prosthesis component, considerable time and development effort has been devoted to tools and techniques to ensure the accurate positioning of the peg holes in the femur. The present invention makes indirect use of these pre-existing tools and techniques in employing the femoral peg holes as the fixation means for the guide portion 6 of the rotary mill 2.

The present invention additionally provides a rotary cutting tool optimised for use with the guide portion 6, the action of which is damped or cushioned, improving ease of use for the surgeon.

The invention claimed is:

1. A rotary mill comprising:
    a body portion having a milling surface and a central bore extending along an axis of rotation of the body portion; and
    a guide portion having a guide body forming a condylar plate and a guide peg extending from the condylar plate and operable to be received in the central bore of the body portion, the guide body having at least one alignment feature which is the same as that of a prosthesis component,
    wherein the guide body includes at least one nodule, protruding from a surface of the condylar plate and operable to abut a corresponding abutment surface on the body portion, the at least one nodule protruding outwardly from the condylar plate.

2. The rotary mill as claimed in claim 1, wherein the at least one alignment feature is an attachment peg.

3. The rotary mill as claimed in claim 2, wherein the guide peg projects from the condylar plate at an angle of approximately between 25 and 40 degrees to an axis of the attachment peg.

4. The rotary mill as claimed in claim 1, wherein the at least one alignment feature is a pair of attachment pegs.

5. The rotary mill as claimed in claim 1, wherein the guide peg comprises an abutment surface operable to abut a corresponding abutment surface in the central bore of the body portion.

6. The rotary mill as claimed in claim 5, wherein the abutment surface comprises a distal surface of the peg.

7. The rotary mill as claimed in claim 5, wherein the abutment surface comprises an outwardly projecting annular shoulder.

8. The rotary mill as claimed in claim 7, wherein the corresponding abutment surface of the central bore comprises an inwardly projecting annular shoulder.

9. The rotary mill as claimed in claim 1, wherein the guide peg projects from a predetermined region of and at a predetermined angle to the guide body.

10. The rotary mill as claimed in claim 1, wherein the guide peg is adjustable on the guide body.

11. The rotary mill as claimed in claim 1, wherein the guide body is operable to be connected to additional surgical tools.

12. The rotary mill as claimed in claim 1, wherein the condylar plate forms a trial femoral prosthesis component.

13. The rotary mill as claimed in claim 12, wherein the guide body is operable to be connected to a posterior osteophyte guide.

14. The rotary mill as claimed in claim 1 wherein the guide body comprises a trial unicondylar femoral prosthesis component.

15. The rotary mill as claimed in claim 14, wherein the guide peg projects from an anterior portion of the guide body.

16. The rotary mill as claimed in claim 15, wherein the guide peg is operable to guide reaming of a region superior to the anterior portion of the guide body.

17. The rotary mill as claimed in claim 1, further comprising additional guide portions, each guide portion being of a different size.

18. The rotary mill as claimed in claim 1, further comprising additional guide portions, each guide portion having a different length or angle of extension of guide peg.

19. A rotary cutting tool comprising;
a rotary body having a cutting surface formed on an annular cutting plate removably attachable to the rotary body, wherein an end of the rotary body terminates in an annular receiving plate having cooperating formations comprising a fastener and a plurality of magnets operable to engage the annular cutting plate and secure the annular cutting plate to the receiving plate; and
a guide shaft at least partially received within the rotary body, wherein the guide shaft comprises an inner portion telescopically received within an outer portion; and
a biasing element acting between the inner and outer portions.

20. The rotary cutting tool as claimed in claim 19, wherein the guide shaft is received within an axial bore formed on the rotary body.

21. The rotary cutting tool as claimed in claim 19, further comprising cooperating protrusions formed on the rotary body and the outer portion of the guide shaft, operable to engage one another as a depth stop.

22. The rotary cutting tool as claimed in claim 19, wherein the biasing element comprises a spring.

23. The rotary cutting tool as claimed in claim 22, wherein the spring is mounted about the inner portion of the guide shaft.

24. The rotary cutting tool as claimed in claim 22, wherein the spring acts between an end of the outer portion of the guide shaft and an end cap formed on the inner portion of the guide shaft.

25. The rotary cutting tool as claimed in claim 24, wherein the end cap is formed by an end of an axial bore in which the guide shaft is received.

26. The rotary cutting tool as claimed in claim 19, wherein the outer portion of the guide shaft comprises a hollow shaft, a first end of which receives the inner portion and a second end of which is operable to receive a guide peg.

27. A rotary mill comprising:
a body portion having a milling surface and a central bore extending along an axis of rotation of the body portion; and
a guide portion having a guide body and a guide peg extending from the guide body, the guide peg operable to be received in the central bore of the body portion, the guide body having at least one alignment feature which is the same as that of a prosthesis component,
wherein the guide body comprises a trial unicondylar femoral prosthesis component and the guide peg projects from an anterior portion of the guide body, the guide peg operable to guide reaming of a region superior to the anterior portion of the guide body.

28. The rotary mill as claimed in claim 27, wherein the body portion comprises a rotary body and a guide shaft at least partially received within the rotary body and the guide shaft comprises an inner portion telescopically received within an outer portion and a biasing element acting between the inner and outer portions.

29. The rotary mill as claimed in claim 28, wherein the biasing element comprises a spring mounted about the inner portion of the guide shaft.

30. The rotary mill as claimed in claim 28, further comprising cooperating protrusions formed on the rotary body and the outer portion of the guide shaft, operable to engage one another as a depth stop.

31. The rotary mill as claimed in claim 28, wherein the outer portion of the guide shaft comprises a substantially hollow shaft, a distal end of which comprises the central bore of the body portion.

32. A rotary mill comprising:
a body portion including a milling surface, a central bore extending along an axis of rotation of the body portion, a rotary body, and a guide shaft at least partially received within the rotary body; and
a guide portion having a guide body forming a condylar plate and a guide peg extending from the condylar plate and operable to be received in the central bore of the body portion, the guide body having at least one alignment feature which is the same as that of a prosthesis component.

33. The rotary mill as claimed in claim 32, wherein the guide shaft comprises an inner portion telescopically received within an outer portion and a biasing element acting between the inner and outer portions.

34. The rotary mill as claimed in claim 33, wherein the biasing element comprises a spring mounted about the inner portion of the guide shaft.

35. The rotary mill as claimed in claim 33, further comprising cooperating protrusions formed on the rotary body and the outer portion of the guide shaft, operable to engage one another as a depth stop.

36. The rotary mill as claimed in claim 33, wherein the outer portion of the guide shaft comprises a substantially hollow shaft, a distal end of which comprises the central bore of the body portion.

37. The rotary mill as claimed in claim 32, wherein the milling surface is formed on an annular cutting tool removably attached to the rotary body.

* * * * *